United States Patent [19]

Masse et al.

[11] Patent Number: 5,397,508
[45] Date of Patent: Mar. 14, 1995

[54] 2-AMINO-5-NITROPYRIDINIUM SALTS USABLE IN NON-LINEAR OPTICS AND IN ELECTROPTICS AND A PROCESS FOR PREPARING THE SAME

[75] Inventors: René Masse, Brignoud; Joseph Zyss, Sceaux, both of France

[73] Assignees: France Telecom Etablissement Autonome de Droit Public (Centre National d'Etudes des Telecommunications), Issy les Moulineaux; Centre National de la Recherche Scientifique, Paris, both of France

[21] Appl. No.: 798,647

[22] Filed: Nov. 26, 1991

[51] Int. Cl.⁶ .................... F21V 9/00; C07D 211/92
[52] U.S. Cl. ..................................... 252/582; 546/347
[58] Field of Search .............. 546/347; 252/582, 587; 359/326, 328

[56] References Cited

U.S. PATENT DOCUMENTS

| 2,676,926 | 4/1954 | Smith et al. | 546/347 |
| 2,909,525 | 10/1959 | Fand | 546/347 |
| 3,101,256 | 8/1963 | Holmberg | 546/347 |
| 3,337,556 | 8/1967 | Kroll | 546/347 |
| 4,150,233 | 4/1979 | Chadwick | 546/347 |

OTHER PUBLICATIONS

Chem. Abst., vol. 99, No. 24, 1983, p. 516, M. Perrin et al.: "Organic Materials for Non-Linear Optics", 203179 g.
Journal of the Chem-Soc., Chem. Comm., No. 23, 1989, pp. 1856–1859; C. B. Aakeroy et al.: "A Novel Class of Salts for Second Harmonic Generation".
Chem. Abst., vol. 112, No. 26, 1990, p. 488, Cheng L. T. et al.: "Nonresident EFISH and THG studies of nonlinear optical property and molecular structure relatives of benzene, stilbene and other arene derivatives".
Hilal et al., CA 94:174101q (1981), see Also Attached Structure–Registry No. 77311–59–2.

Primary Examiner—Philip Tucker
Attorney, Agent, or Firm—Oblon, Spivak, McClelland, Maier, & Neustadt

[57] ABSTRACT 2-amino-5-nitropyridinium salts are provided which are usable in non-linear and electrooptics.

9 Claims, 1 Drawing Sheet

2-AMINO-5-NITROPYRIDINIUM SALTS USABLE IN NON-LINEAR OPTICS AND IN ELECTROPTICS AND A PROCESS FOR PREPARING THE SAME

BACKGROUND OF THE INVENTION

1. Field of the Invention

The present invention relates to 2-amino-5-nitropyridinium salts usable in non-linear optics and in electrooptics.

2. Description of the Background

By the term "nonlinear optics," is meant the field of optics which extends from the conversion of optical frequencies, i.e., obtaining an optical radiation from two radiations of different frequencies, the frequency of the conversion radiation being equal to the sum or to the difference of the frequencies of the two radiations or conversely, breakdown of an incident beam into two beams of low frequencies, to electrooptical modulation, i.e., modification of one of the radiation characteristics by application of an electric field to a crystal through which the radiation passes.

Many materials likely to be suitable for the conversion of optical frequencies or for the electrooptical modulation are already known. Of the latter, mineral materials such as potassium diphosphate (KDP), lithium niobate and potassium titanium oxide monophosphate (KTP) may be mentioned.

However, these mineral materials are, in fact, not effective, which necessitates using them in large thicknesses. For several years, research has been conducted relating to the production of crystals of organic molecules exhibiting an improved effectiveness relative to the inorganic crystals of potassium diphosphate or lithium niobate. Thus, as described by J. Zyss in Current Trends in Optics, Taylor & Francis, London, 1981, pp. 122-134, it was found that the aniline or pyridine-N-oxide derivatives such as metanitroaniline (mNA), 2-methyl-4-nitroaniline (MNA), methyl 2(2,4-dinitrophenyl)-aminopropanoate and 3-methyl-4-nitropyridine-1-oxide (POM) that are the object of FR-A-2 472 201 may be used for this purpose.

In EP-A- 0 091 838, the advantageous properties of the optionally deuterated N-(4-nitrophenyl)-L-prolinol (NPP) are also described.

Recently, in Zeitschrift fuer Kristallogr. 190, 1990, pp. 19-32, R. Masse and A. Durif proposed new piezoelectric and ferroelectric crystals, usable in nonlinear optics, consisting of methylalaninium diacid monophosphates. These monophosphates are polar materials with a mineral anionic framework, using polyanion $(H_2PO_4^-)_n$ in the form of layers inside which organic cations are placed.

The search for salts for quadratic nonlinear optics, in which cations exhibiting a nature of intramolecular charge transfer and coupling are associated with chiral, achiral or mineral organic anions, has also been developed by G. R. Meredith (ACS symposium series 233, 1983, pp. 27-56). In this case, the object is to, at once, obtain:

1) a noncentrosymmetric stack of achiral organic cations in a crystalline structure, and
2) an optimal orientation of these cations (charge transfer axis) relative to the dielectric axes of the crystal, making it possible to assure the birefringence necessary for the agreement of phases between the interacting beams, for each class of symmetry according to J. Zyss and J. L. Oudar (Pys. Rev. A 26, 2028, 1982).

Thus, two large families of materials have been the object of intensive research conducted independently until now, i.e., the mineral monocrystals, on the one hand, and the organic molecular crystals, on the other hand.

Each of these families exhibits advantages and drawbacks connected to such parameters as:

1) the nonlinear effectiveness, i.e., parametric or electrooptic figure of merit,
2) the extent of the transparency range,
3) the optical damage threshold, i.e., under continuous radiation or radiation by pulse,
4) the mechanical qualities, i.e., hardness, strength, tendency to cleavage, density of dislocations, capacity for cutting and polishing,
5) the chemical or physicochemical stability, i.e., photoreactivity, stability in air, hygroscopy, tendency to sublimation, and
6) the capacity for crystal growth, i.e., solubility, stability in melting, initial purity.

Unfortunately, with respect to these various parameters, neither of the two families is completely satisfactory. Some crystalline organic materials are known for their figures of merit (parametric gain or half-wave voltage) that are clearly higher than those of their mineral equivalents. Thus, N-(4-nitrophenyl)-L-prolinol (NPP) has a parametric gain that is greater by two orders of magnitude than that of potassium titanium oxide monophosphate (KTP). However, the mineral oxides such as KTP appear to resist better the laser irradiation in continuous flux.

The organic materials studied to date in general appear to exhibit an optimum of the effectiveness-transparency compromise on the whole centered in the near infrared. However, the cohesion of the ionic mineral cages is greater than that of the molecular crystals associated by less energetic Van Der Waals forces. It is therefore possible to expect better mechanical properties. Moreover, the increase in aqueous solution of bulky mineral crystals, for example, potassium diacid monophosphate (KDP) is now a well-established industrial reality.

Clearly, a need exists for organic cation salts exhibiting the advantages of two types of materials, either, on the one hand, the high polarizabilities of organic molecules and the possibility, by virtue of chemical substitutions, of inducing high nonlinear capacities and, on the other hand, the cohesion and the strength of the stacks of the anionic cages of mineral oxides. To date, however, such organic cation salts are unknown.

SUMMARY OF THE INVENTION

Accordingly, it is an object of the present invention to provide certain 2-amino-5-nitropyridinium salts which exhibit the above-described desired properties.

It is also an object of the present invention to provide deuterated 2-amino-5-nitropyridinium salts having such desirable properties.

It is, further, an object of the present invention to provide a process for preparing the 2-amino-5-nitropyridinium salts of the present invention.

Accordingly, the above objects and others which will become more apparent in view of the following disclosure are provided by 2-amino-5-nitropyridinium salts of the formula:

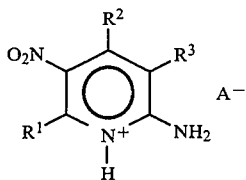

wherein A⁻ represents an inorganic anion selected from the group consisting of $H_2PO_4^-$, $HSO_4^-$ and $H_2AsO_4^-$; and $R^1$, $R^2$ and $R^3$, which are identical to or different from each other, are H or $CH_3$.

DETAILED DESCRIPTION OF THE PREFERRED EMBODIMENTS

Figure 1:
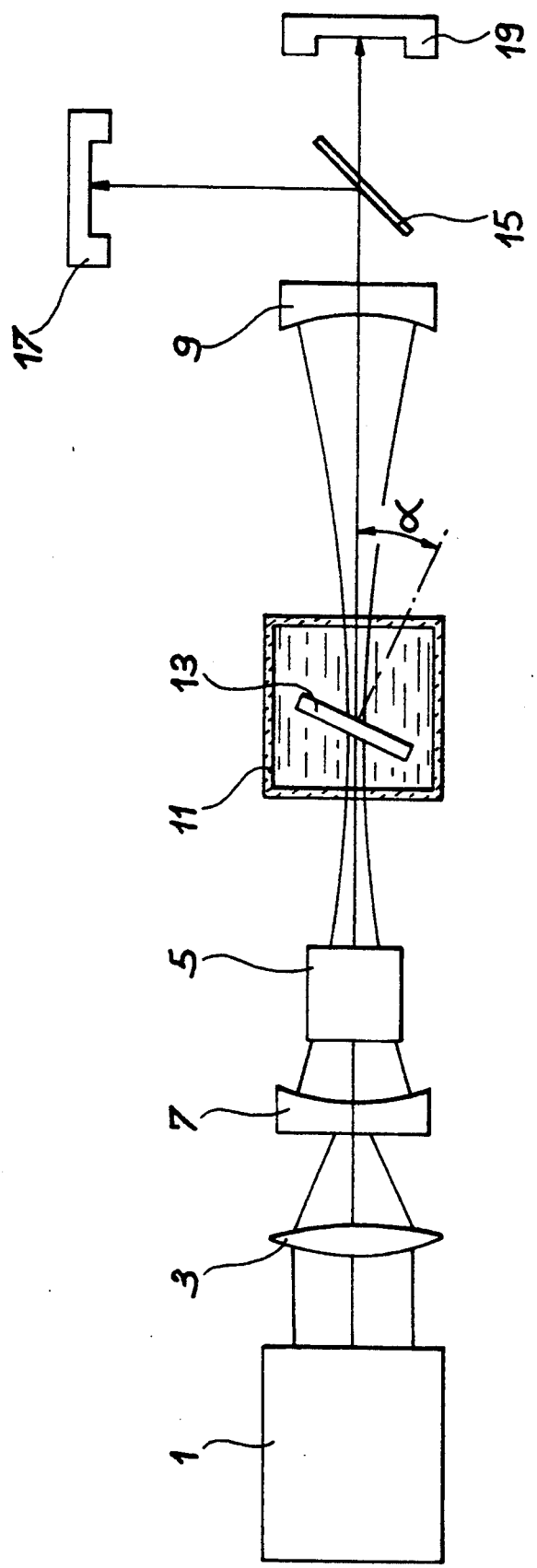
FIG. 1 diagrammatically represents a frequency doubler device using a salt crystal in accordance with the present invention.

In accordance with the present invention, 2-amino-5-nitropyridinium salts are provided having the formula:

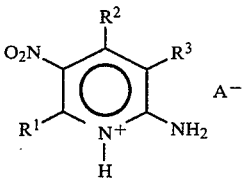

in which A⁻ represents an inorganic anion selected from the group consisting of $H_2PO_4^-$, $HSO_4^-$ and $H_2AsO_4^-$, and $R^1$, $R^2$ and $R^3$ which are identical or different from each other, are H or $CH_3$.

These salts can also be partially or totally deuterated. In this case, at least one of the hydrogen atoms of above-mentioned formula (I) is replaced by a deuterium atom.

By way of example, it is possible to cite the 2-amino-5-nitropyridinium diacid monophosphate, corresponding to formula (Ia)

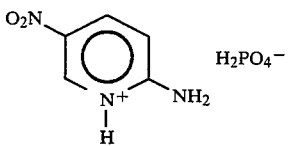

as well as the partially or totally deuterated derivatives of this salt.

The organomineral salts of the invention are very advantageous because of their particular structure in which the organic cations, carriers of a significant dipolar moment and whose spectrum comprises an intramolecular charge transfer state predominant in the visible region or the near infrared, are anchored by hydrogen bonds between the $(A^-)_n$ mineral polyanion layers such as $(H_2PO_4^-)_n$.

In accordance with the present invention, the selection of a 2-amino-5nitropyridinium cation, or a pyridinic derivative of paranitroaniline, obtained by replacing the CH group in the "ortho" position of the electron-donor amino grouping of the pnitroaniline by a nitrogen, makes it possible to perform the anchoring and the insertion of the cation by a hydrogen bond on the mineral anions by a proton attracted to the same site. Thus, passage is made from one standard entity in nonlinear optics, paranitroaniline, to a molecule that is also effective in nonlinear optics, more transparent and able to be linked easily by hydrogen bonds to a chain of mineral anions.

2-amino-5-nitropyridine, which is a neutral compound, was previously known, however, the centrosymmetric structure of the corresponding molecular crystal prohibited any use of it in nonlinear optics for the effects of the second order.

According to the present invention, the complexing, in an ionic crystalline network, of this molecule with a polyanionic chain makes it possible to achieve a nonlinear effectiveness quite superior to that of known organomineral crystals such as the compounds described by AAKEROY et al. in Journal of the Chemical Society Chemical Communications, no. 23, 1989, p. 1857, whose effectiveness is inferior to that of urea since the better compound does not exceed quartz five times.

In the present invention, the selection of the mineral anion, $H_2PO_4^-$, $HSO_4^-$ or $H_2AsO_4^-$, makes it possible to take advantage of the steric and chemical modularity of these ionic mineral structures, and their stability for forming a stable and structuralized inorganic subnetwork, able to fix and optionally to orient and polarize the 2-amino-5-nitropyridinium cations.

Moreover, because of these two selections, there is a chemical compatibility between the organic and mineral units of the compound and a miscibility with a high organic concentration. Also, the underlying electronic properties in the nonlinearity of the paranitroaniline (transparency, coupling, charge transfer) are maintained or improved; and a compound which can be put easily into the form of monocrystals, having a noncentered structure, is obtained.

Thus, in the salt of the present invention, the stack of achiral organic cations is determined by the two-dimensional structure of the subnetwork of mineral anions, consisting, for example, of strongly dipolar $H_2PO_4^-$ units. This subnetwork has a specific cohesion due to short hydrogen bonds, that would not be able to compromise the associated organic cations ("guest/host" structure) and the overall cohesion of the crystalline structure is assured by a system of hydrogen bonds. Therefore, the favorable characteristics of stability and thermal conductivity of the KDP are found in these crystals. The $(H_2PO_4^-)_n$ anion has a stability comparable to that of the organic cations that are associated with it. The salts of the present invention can be prepared by a simple process consisting in causing a 2-amino-5-nitropyridine of formula:

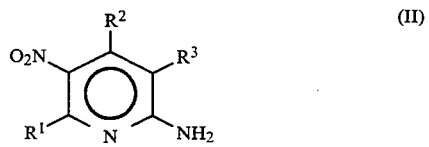

to react in which $R^1$, $R^2$ and $R^3$ have the meaning given above, with the acid of formula $A^-H^+$ in which $A^-$ has the meaning given above.

Generally, the process is performed in aqueous solution by using an excess of acid $A^-H^+$ for example, 3 mol of acid per mol of 2-amino-5-nitropyridine as the excess acid is favorable to the dissolution of pyridine in water.

Since the reaction takes place in water, there is a competition between the basicity of the water with formation of $H_3O^+$ and that of 2-amino-5-nitropyridine, which is a particularly weak base.

It is also possible to prepare the salt directly, protected from air without excess water or in air by expelling the water.

When it is desired to prepare the partially or totally deuterated salt, the salt obtained previously is then subjected to a deuteration.

The deuteration operation can be performed by standard isotopic exchange methods, for example, by exchange with heavy water $D_2O$, by reaction with DCl and $AlCl_3$, by extended treatment in the presence of $D_2SO_4$ or by treatment in deuterated liquid ammonia in the presence of sodium as catalyst. These methods are described in "Isotopic Exchange and the Replacement of Hydrogen in Organic Compounds" A. I. Shatenshtein Consultant Bureau N. Y. (1962), Appendix pp. 295–308.

Moreover, it is also possible to obtain deuterated salts by synthesis by causing a partially or totally deuterated 2-amino-5-nitropyridine of formula (II) to react with the optionally deuterated acid of formula $A^-H^+$.

The deuterated 2-amino-5-nitropyridine can be prepared from 2-amino-5-nitropyridine of formula (II) by the deuteration processes described above.

The 2-amino-5-nitropyridine of formula (II) can be prepared by standard processes.

The 2-amino-5-nitropyridinium salts of the invention can easily be put into the form of monocrystals by crystalline growth in aqueous solution of phosphoric acid by using, for example, one of the processes described below.

First, a process may be used using a reactor with a single compartment according to which a crystal nucleus of the salt is dipped in a crystallizer, attached to a glass rod in rotation, in a saturated solution of the salt in the phosphoric acid. The temperature of the crystallizer is kept constant and the hygrometric degree of the atmosphere above the crystallizer is controlled so that the evaporation is neither too quick nor too slow. The temperature can be lowered to reduce the solubility when the crystalline growth slows down. The obtained crystal is taken out and dipped again in a crystallizer whose solution has the same characteristics as the initial solution until the optimal size is reached.

Second, a process may be used using a glass reactor with a double compartment according to which a crystal of the salt is made to rotate in a compartment of the reactor containing a saturated solution of the salt and this solution is enriched in proportion as the crystal grows at the expense of a saturated solution which comes from the other compartment, kept at higher temperature in which a crystalline powder of the salt is continuously dissolved. The solution circulates from one compartment to the other under the effect of a thermal gradient which maintains a concentration gradient.

The optically pure salts of the present invention may be widely used in the field of quadratic nonlinear optics and corresponding uses. Thus, they can be used in devices for: second harmonic generation (SHG), the addition of frequencies (or "up-conversion"), optical parametric emission, optical parametric amplification, optical parametric oscillation (OPO), etc., electrooptical or Pockels-effect modulation, and the conversion of infrared frequencies to visible frequencies.

In the latter case, the precise nature of the device and field of applications will depend on the transparency windows of the salt. Thus, salts transparent in the visible region and up to 400 nm will be suitable for the conversion to blue of laser diodes emitting to 850 nm, the main application being the production of sources for high-density optical memories. For applications such as the detection and the measurement of the time characteristics of brief light impulses in the near infrared (1.5 microns) by selfcorrelation, a lower transparency such as that of the analogues of paranitroaniline can be suitable.

Further, the present salts may also be used for the detection and the time resolution of brief impulses by selfcorrelation (generation of frequencies) or "up-conversion" (sum of frequencies), the production of coherent sources that are tunable in the near infrared and the amplification of their radiations, wide-band modulators for telecommunications or the optical processing of the signal (directional coupler, optical switching point), and the generation of compressed states ("squeezed states") of light with optimal noise characteristics.

It is also possible to use the salts of the invention for their ferroelectric, piezoelectric and pyroelectric properties in many devices such as memories, sensors, and transducers acting under the effect of temperature, pressure, an electric voltage or an optical irradiation.

For nonlinear optics applications, the present salts in the optically pure state can be used in various forms, for example, in the form of powders, in the form of inclusions of molecules in a host network (polymer, clathrate, solid solution), in the form of thin layers deposited on a substrate, in the form of monocrystal, in the form of solutions, etc.

Generally, they are first purified, then put in the desired form, for example, in the form of monocrystals, by standard processes, for example, by evaporation of solvent or by a method of growth in solution by controlled cooling. When it is desired to use them in the form of thin layers, it is possible to prepare such layers by Langmuir-Blodgett method or else by epitaxy.

The present invention will now be further illustrated by reference to certain examples which are provided for purposes of illustration and are not intended to be limitative.

EXAMPLE

This example relates to the preparation and the Use of 2-amino-5-nitropyridinium diacid monophosphate (2A5NPDP), or the salt of formula (Ia).

1 mol of 2-amino-5-nitropyridine is dissolved in 50 cm3 of an aqueous solution containing 3 mol of phosphoric acid at a temperature of 60° C. Thus, 2-amino-5-nitropyridinium diacid monophosphate (2A5NPDP) is obtained in solution.

Then, salt crystals are prepared from this solution by evaporation in air, which gives fine 2A5NPDP crystals of a 5 to 12 mm length and a 4 mm width, of a slightly yellow color.

It is also possible to obtain very fine and very pure white 2A5NPDP crystals by precipitation of a saturated 2A5NPDP solution, at equilibrium, by ethyl alcohol. A white powder is thus obtained which does not dissolve in water but in an acid solution at 60° C. containing at least 2 mol of $H_3PO_4$ per 1 mol of 2-amino-5-nitropyridinium diacid monophosphate (2A5NPDP).

The 2A5NPDP is easily broken down by warm water in $H_3PO_4$ and in 2-amino-5-nitropyridine.

The crystalline structure of the powder is determined by x-ray crystallography and it is observed that the powder has a polar crystalline structure (spatial group $Pna2_1$, specific group $mm_2$), and is compatible both with the nonlinear optic requirements (quadratic effects) and ferroelectricity.

The standard second-harmonic generation test is performed on the powder of the previously obtained salt according to the method described by: S. K. Kurtz and T. T. Perry in J. Appl. Phys., 39, pp. 37–98, (1968), by using a 2A5NPDP powder with grains calibrated between 100 and 200 microns of average radius after successive siftings, a YAG laser at 1.06 micron and the harmonic at 530 nm. Under these conditions, the 2-amino-5- nitropyridinium diacid monophosphate powder of the invention emits a green radiation with an effectiveness on the order of that of 3-methyl-4-nitropyridine-1-oxide (POM) (slightly lower) and on the order of 10 times that of urea.

Thus, the 2A5NPDP exhibits an intermediate nonlinear response between that of urea and that of POM which are organic crystals much used in nonlinear optics because of their good compromise between the transparency and the effectiveness (centered on the near ultraviolet for urea and on the near infrared for POM).

The transparency of the 2-amino-5-nitropyridinium diacid monophosphate (2A5NPDP) crystals of the invention is intermediate between that of urea and of POM with an absorption limit in the solid state toward 300 nm (200 nm for urea and 460 nm for POM).

The crystals thus have an intermediate transparency range between that of the purely mineral compound KDP and that of monocrystals consisting of molecular units similar to paranitroaniline.

The effectiveness of conversion of the basic radiation to harmonic radiation profits from the input of a double network of anharmonic oscillators in interaction: one attached to the 2-amino-5-nitropyridinium organic cation, the other to the $H_2PO_4^-$ mineral anion.

By way of example, the use of this 2-amino-5-nitropyridinium diacid monophosphate crystal in an intracavity frequency doubler similar to that described by Ducharme et al. in Appl. Phys. Lett. 57(6), 1990, pp. 537–539, is described below.

Such a frequency doubler device is represented diagrammatically in FIG. 1 and comprises a titanium-sapphire laser emitting to 900 nm, i.e., in the transparency range of the 2A5NPDP, and a 2A5NPDP crystal placed in the inner cavity of this laser.

In FIG. 1, it is seen that the device comprises a pumping laser (1), a lens (3) to focus the beam of the laser on a titanium-sapphire element (5) placed between a reflector (7) and an output coupler (9) each comprising a coating to assure respectively a reflection of 100% and 99.5% in the wavelength of 450 nm. Titanium-sapphire element (5) is provided with an antireflective coating for the same wavelength. A basin (11) provided with antireflective coatings for wavelengths of 900 nm and 450 nm, filled with an inert and noncorrosive liquid (for example, of freon type), having an index of refraction making possible a certain optical adaptation (index on the order of 1.5) and containing a crystal (13) of 2A5NPDP oriented to phase agreement angle a, is placed between element (5) and output coupler (9).

A dichroic mirror (15) placed behind output coupler (9) makes it possible to separate the output beam from the laser to direct the basic beam (900 nm) to first detector (17) and second harmonic (450 nm) to second detector (19).

Having described the present invention, it will now be apparent to one of ordinary skill in the art that many changes and modifications may be made to the above-described embodiments without departing from the spirit and scope of the present invention.

What is claimed as new and desired to be secured by LETTERS PATENT of the United States is:

1. 2-amino-5-nitropyridinium salts having the formula:

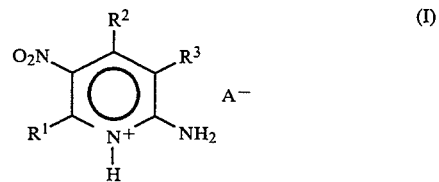

wherein $A^-$ represents an inorganic anion selected from the group consisting of $H_2PO_4^-$, $HSO_4^-$ and $H_2AsO_4^-$; and $R^1$, $R^2$ and $R^3$, which are identical or different from each other, each represents H or $CH_3$.

2. The salts of claim 1 wherein $A^-$ is $H_2PO_4^-$.

3. The salts of claim 1, which are in the form of monocrystals.

4. Deuterated 2-amino-5-nitropyridinium salts having the formula:

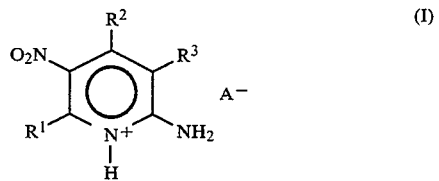

wherein $A^-$ represents an anion selected from the group consisting of $H_2PO_4^-$, $HSO_4^-$ and $H_2AsO_4^-$; and $R^1$, $R^2$ and $R^3$, which are identical or different from each other, each represents H or $CH_3$, and wherein at least one of the hydrogen atoms is replaced by a deuterium atom.

5. The 2-amino-5-nitropyridinium salts of claim 4, having the formula:

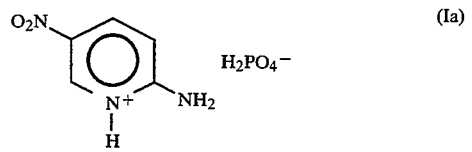

6. The salts of claim 4, wherein $A^-$ is $H_2PO_4^-$.

7. The salts of claim 4, which are in the form of monocrystals.

8. An optical or optoelectric device for second harmonic generation, comprising one or more of the salts of claim 1 or 4.

9. The optical or optoelectric device of claim 8, wherein the salt used is that wherein $A^-$ is $H_2PO_4^-$.

* * * * *

UNITED STATES PATENT AND TRADEMARK OFFICE
CERTIFICATE OF CORRECTION

PATENT NO. : 5,397,508
DATED : March 14, 1995
INVENTOR(S) : Rene MASSE, et al.

It is certified that error appears in the above-indentified patent and that said Letters Patent is hereby corrected as shown below:

On the title page, insert item [30]: Foreign Application Priority Data as follows:

--Nov. 26, 1990 [FR] France.........90 14743--

Signed and Sealed this

Twentieth Day of June, 1995

Attest:

BRUCE LEHMAN

*Attesting Officer*     *Commissioner of Patents and Trademarks*